US009155305B2

(12) United States Patent
Gary

(10) Patent No.: US 9,155,305 B2
(45) Date of Patent: Oct. 13, 2015

(54) ACTIVE COMPOUNDS COMBINATIONS COMPRISING PROTHIOCONAZOLE AND FLUXAPYROXAD

(75) Inventor: Stephanie Gary, Champagne au Mont d'or (FR)

(73) Assignee: BAYER INTELLECTUAL PROPERTY, Monheim (DE)

( * ) Notice: Subject to any disclaimer, the term of this patent is extended or adjusted under 35 U.S.C. 154(b) by 0 days.

(21) Appl. No.: 13/812,858

(22) PCT Filed: Aug. 2, 2011

(86) PCT No.: PCT/EP2011/063268
§ 371 (c)(1),
(2), (4) Date: Apr. 5, 2013

(87) PCT Pub. No.: WO2012/016972
PCT Pub. Date: Feb. 9, 2012

(65) Prior Publication Data
US 2013/0184152 A1   Jul. 18, 2013

(30) Foreign Application Priority Data
Aug. 5, 2010   (EP) ..................... 10172028

(51) Int. Cl.
*A01N 43/56* (2006.01)
*A01N 43/653* (2006.01)
(52) U.S. Cl.
CPC .............. *A01N 43/653* (2013.01); *A01N 43/56* (2013.01)
(58) Field of Classification Search
USPC ................................... 504/100; 514/384, 406
See application file for complete search history.

(56) References Cited

U.S. PATENT DOCUMENTS

| 4,245,432 | A | 1/1981 | Dannelly |
| 4,272,417 | A | 6/1981 | Barke et al. |
| 4,808,430 | A | 2/1989 | Kouno |
| 5,789,430 | A | 8/1998 | Jautelat et al. |
| 5,859,039 | A | 1/1999 | Jautelat et al. |
| 5,876,739 | A | 3/1999 | Turnblad et al. |
| 2003/0176428 | A1 | 9/2003 | Schneidersmann et al. |
| 2008/0293798 | A1* | 11/2008 | Dietz et al. ............... 514/407 |

FOREIGN PATENT DOCUMENTS

| CN | 101257798 A | 9/2008 |
| CN | 102595903 A | 7/2012 |
| WO | 9616048 A1 | 5/1996 |
| WO | 02/28186 A2 | 4/2002 |
| WO | 02/080675 A1 | 10/2002 |
| WO | 2006087343 A1 | 8/2006 |
| WO | 2007003643 A1 | 1/2007 |
| WO | 2007017416 A2 | 2/2007 |
| WO | 2007/027777 A2 | 3/2007 |
| WO | 2009098218 A2 | 8/2009 |
| WO | 2009098223 A2 | 8/2009 |
| WO | 2012019981 A1 | 2/2010 |
| WO | 2010139653 A1 | 12/2010 |
| WO | 2010145999 A2 | 12/2010 |

OTHER PUBLICATIONS

International Search Report and Written Opinion of International Application No. PCT/EP2011/063268, mailed on Feb. 14, 2013.
Colby, S.R., "Calculating Synergistic and Antagonistic Responses of Herbicide Combinations," Weeds 15(1):20-22 (Jan. 1967).
Tammes, P.M.L. "Isoboles, A Graphic Representation of Synergism in Pesticides," Neth. J. Plant. Path. 70:73-80 (1964).
Draber, W. and R. Wegler, "Gibberelline," Chemie der Pflanzenschutz- und Schädlingsbekämpfungsmittel, Literatur s. S. 410, pp. 401-412 (1970).
Internatioinal Search Report for PCT/EP2011/063268 Mailed March 13, 2012.

* cited by examiner

*Primary Examiner* — John Pak
(74) *Attorney, Agent, or Firm* — Miles & Stockbridge P.C.

(57) ABSTRACT

The present invention relates to active compound combinations, in particular within a fungicide composition, which comprises (A) prothioconazole and (B) fluxapyroxad and optionally (C) a further fungicidally active compound. Moreover, the invention relates to a method for curatively or preventively controlling the phytopathogenic fungi of plants or crops (e.g. cereals such as wheat, barley, rye, oats, millet and triticale; soya beans; rice; com/maize; oil seed rape including canola; beans, peas, peanuts; sugar beet, fodder beet, beetroot; potatoes; cotton), and to the use of a combination according to the invention for the treatment of seed, to a method for protecting a seed and not at least to the treated seed.

8 Claims, No Drawings

ACTIVE COMPOUNDS COMBINATIONS COMPRISING PROTHIOCONAZOLE AND FLUXAPYROXAD

CROSS REFERENCE TO RELATED APPLICATIONS

This application is a §371 National Stage Application of PCT/EP2011/063268, filed Aug. 2, 2011, which claims priority to European Application No. 10172028.2 filed Aug. 5, 2010.

BACKGROUND OF THE INVENTION

1. Field of the Invention

The present invention relates to active compound combinations, in particular within a fungicide composition, which comprises (A) prothioconazole and (B) fluxapyroxad and optionally (C) a further fungicidally active compound. Moreover, the invention relates to a method for curatively or preventively controlling the phytopathogenic fungi of plants or crops (e.g. cereals such as wheat, barley, rye, oats, millet and triticale; soya beans; rice; com/maize; oil seed rape including canola; beans, peas, peanuts; sugar beet, fodder beet, beetroot; potatoes; cotton), and to the use of a combination according to the invention for the treatment of seed, to a method for protecting a seed and not at least to the treated seed.

2. Description of Related Art

Prothioconazole (CAS Registry No. 178928-70-6), having the chemical name 2-[2-(1-chlorocyclopropyl)-3-(2-chlorophenyl)-2-hydroxypropyl]-1,2-dihydro-3H-1,2,4-triazole-3-thione (Compound A) and its manufacturing process is described in WO 96/16048.

Fluxapyroxad (CAS Registry No. 907204-31-3), having the chemical name 3-(difluoromethyl)-1-methyl-N-(3',4',5'-trifluorobiphenyl-2-yl)pyrazole-4-carboxamide (Compound B) and its manufacturing process is described in WO 2006/087343.

Certain plant health compositions are also known (WO 2009/098218).

Since the environmental and economic requirements imposed on modern-day crop protection compositions are continually increasing, with regard, for example, to the spectrum of action, toxicity, selectivity, application rate, formation of residues, and favourable preparation ability, and since, furthermore, there may be problems, for example, with resistances, a constant task is to develop new compositions, in particular fungicidal agents, which in some areas at least help to fulfil the abovementioned requirements.

SUMMARY

The present invention provides active compound combinations/compositions which in some aspects at least achieve the stated objective.

It has now been found, surprisingly, that the combinations according to the invention not only bring about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the combination still achieves a high degree of phytopathogen control even where the two individual compounds have become totally ineffective in such a low application rate range. This allows, on the one hand, a substantial broadening of the spectrum of phytopathogens that can be controlled and, on the other hand, increased safety in use.

DETAILED DESCRIPTION OF A PREFERRED EMBODIMENT

In addition to the fungicidal synergistic activity, the active compound combinations according to the invention have further surprising properties which, in a wider sense, may also be called synergistic, such as, for example: broadening of the activity spectrum to other phytopathogens, for example to resistant strains of plant diseases; lower application rates of the active compounds; sufficient control of pests with the aid of the active compound combinations according to the invention even at application rates where the individual compounds show no or virtually no activity; advantageous behaviour during formulation or during use, for example during grinding, sieving, emulsifying, dissolving or dispensing; improved storage stability and light stability; advantageous residue formation; improved toxicological or ecotoxicological behaviour; improved properties of the plant, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compound combinations or compositions according to the invention contributes considerably to keeping young cereal stands healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher long term efficacy of the fungicidal action.

In particular the present invention provides advantageous uses of the combination according to the invention which comprises (A) prothioconazole and (B) fluxapyroxad and optionally (C) a further fungicidally active compound against specific pathogens and in specific crops.

Compound (C) may be selected from the following groups:
(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-P, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy] phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl] 1H-imidazole-1-carbothioate.

(2) Inhibitors of the respiratory chain at complex I or II, for example bixafen, boscalid, carboxin, diflumetorim, fenfuram, fluopyram, flutolanil, furametpyr, furmecyclox, isopyrazam (mixture of syn-epimeric racemate 1RS,4SR, 9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and salts thereof.

(3) Inhibitors of the respiratory chain at complex III, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}-amino)oxy]methyl}phenyl)ethanamide, (2E)-2-(methoxyimino)-N-methyl-2-{2-[(E)-({1-[3-(trifluoromethyl)-phenyl]ethoxy}imino)methyl]phenyl}ethanamide, (2E)-2-{2-[({[(1E)-1-(3-{[(E)-1-fluoro-2-phenylethenyl]-oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methyl-ethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethyl-phenoxy)methyl]phenyl}-2-methoxy-N-methylacetamide and salts thereof.

(4) Inhibitors of the mitosis and cell division, for example benomyl, carbendazim, chlorfenazole, diethofencarb, ethaboxam, fluopicolide, fubecridazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine, 3-chloro-5-(6-chloro-pyridin-3-yl)-6-methyl-4-(2,4,6-trifluorophenyl) pyridazine and salts thereof.

(5) Compounds capable to have a multisite action, like for example bordeaux mixture, captafol, captan, chlorothalonil, copper hydroxide, copper naphthenate, copper oxide, copper oxychloride, copper(II) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb, ziram and salts thereof.

(6) Compounds capable to induce a host defence, like for example acibenzolar-S-methyl, isotianil, probenazole, tiadinil and salts thereof.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and salts thereof.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon and tricyclazole.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, like for example binapacryl, dinocap, ferimzone, fluazinam and meptyldinocap.

(15) Further compounds, like for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezinc, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrrolnitrin, tebufloquin, tecloftalam, tolnifanide, triazoxide, trichlamide, zarilamid, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl) pyridine, 2,3-dibutyl-6-chlorothieno[2,3-d]pyrimidin-4 (3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-

(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyf)methylidene]amino}oxy)methyl]pyridin-2-yl}-carbamate, phenazine-1-carboxylic acid, quinolin-8-ol and quinolin-8-ol sulfate (2:1).

(16) Further compounds like for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoro-methyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methyl-phenyl)methanone and N-[2-(4-{[3-(4-chlorophenyl)prop-2-yn-1-yl]oxy}-3-methoxyphenyl)ethyl]-N2-(methyl-sulfonyl)valinamide.

If the active compounds in the active compound combinations according to the invention are present in certain weight ratios, the synergistic effect is particularly pronounced. However, the weight ratios of the active compounds in the active compound combinations can be varied within a relatively wide range.

In the combinations according to the invention the compound (A) and (B)—and if applicable the compounds (A) and (C)—are present in a synergistically effective weight ratio of A:B—and if applicable A:C—in a range of 100:1 to 1:100, preferably in a weight ratio of 50:1 to 1:50, most preferably in a weight ratio of 20:1 to 1:20. Further ratios of A:B—and if applicable A:C—which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) and optionally compound (C) can be present in tautomeric form, such a compound is understood hereinabove and hereinbelow also to include, where applicable, corresponding tautomeric forms, even when these are not specifically mentioned in each case.

Compound (A) or compound (B) and optionally compound (C) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Compound (A) or compound (B) and optionally compound (C) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compound (A) or the compound (B) and optionally compound (C) in free form and in the form of their salts, hereinabove and herein below any reference to the free compound (A) or free compound (B) and optionally compound (C) or to their salts should be understood as including also the corresponding salts or the free compound (A) or free compound (B) and optionally free compound (C), respectively, where appropriate and expedient. The equivalent also applies to tautomers of compound (A) or compound (B) and optionally compound (C) and to their salts.

According to the invention the expression "combination" stands for the various combinations of compound (A) and (B) and optionally compound (C), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compound (A) and (B) and optionally compound (C) is not essential for working the present invention.

In conjunction with the present invention "controlling" denotes a significant reduction of the infestation of a disease in comparison to the untreated crop, more preferably the infestation is essentially diminished (50-79%), most preferably the infestation is totally suppressed (80-100%).

The present invention furthermore relates to compositions for combating/controlling undesirable microorganisms comprising the active compound combinations according to the invention. Preferably, the compositions are fungicidal compositions comprising agriculturally suitable auxiliaries, solvents, carriers, surfactants or extenders.

Furthermore the invention relates to a method of combating undesirable microorganisms, characterized in that the active compound combinations according to the invention are applied to the phytopathogenic fungi and/or their habitat.

One embodiment of the present invention relates to the use of the composition, which comprises (A) prothioconazole and (B) fluxapyroxad for controlling wheat diseases caused by *Alternaria* spp., in particular *Alternaria triticina, Aschochyta tritici, Athelia rolfsi, Bipolaris sorokiniana, Blumeria graminis, Cephalosporium gramineum, Ceratobasidium cereale, Cladosporium* spp., in particular *Cladosporium herbarum, Clathrospora pentamera, Claviceps purpurea, Cochliobolus sativus, Colletotrichum graminicola, Coprinus psychromorbidus, Dilophospora alopecuri, Drechslera campanulata, Drechslera tritici-repentis, Drechslera wirreganesis, Epicoccum* spp., *Erysiphe graminis, Fusarium avenaceum, Fusarium culmorum, Fusarium graminearum, Fusarium pseudograminearum, Gaeumannomyces graminis, Gaeumannomyces graminis* var. *avenae, Gaeumannomyces graminis* var. *tritici, Gibberella avenacea, Gibberella zeae, Gibellina cerealis, Glomerella graminicola, Hymenula cerealis, Lagena radicicola, Leptosphaeria herpotrichoides, Leptosphaeria microscopica, Leptosphaeria nodorum, Ligniera pilorum, Linochora graminis, Microdochium bolleyi, Microdochium nivale, Monographella nivalis, Mycosphaerella graminicola, Oidium monilioides, Olpidium brassicae, Phaeosphaeria avenaria* f. sp. *triticea, Phaeosphaeria nodorum, Phoma sorghina, Phoma glomerata, Phyllachora graminis, Pseudocercosporella herpotrichoides* var. *acuformis, Pseudocercosporella herpotrichoides, Puccinia graminis, Puccinia hordei, Puccinia recondita, Puccinia striiformis, Puccina tritici-duri, Puccinia triticina, Pyrenophora graminea, Pyrenophora semeniperda, Pyrenophora teres, Pyrenophora tritici-repentis, Pythium myriotylum, Pythium aphanidermatum, Pythium aristosporum, Pythium arrhenomanes, Pythium graminicola, Pythium iwayamai, Pythium okanoganense, Pythium volutum, Rhizoctonia cerealis, Rhizoctonia solani, Rhizophydium graminis, Sclerophthora macrospore, Sclerotinia borealis, Sclerotium rolfsii, Sclerotium rolfsii, Selenophoma donacis, Septoria nodorum, Septoria tritici, Sphacelia segetum, Sporobolomyces* spp., *Stagonospora avenae* sp. *tritica, Stemphylium* spp., *Tapesia yallundae, Thanatephorus cucumeris, Tilletia caries, Tilletia controversa, Tilletia foetida, Tilletia indica* (=*Neovossia indica*), *Tilletia laevis, Typhula idahoensis, Typhula incarnata, Typhula ishikariensis* Imai var. *canadensis, Typhula ishikariensis, Uredo glumarum, Urocystis agropyri, Ustilago segetum avena, Ustilago segetum nuda, Ustilago segetum tritici, Ustilago tritici.*

Another embodiment of the present invention relates to the use of the composition, which comprises (A) prothioconazole and (B) fluxapyroxad and (C) a further fungicidally active compound for controlling wheat diseases caused by the above mentioned organisms.

Another embodiment of the present invention relates to the use of the composition, which comprises (A) prothioconazole and (B) fluxapyroxad for controlling barley diseases caused by *Alternaria* spp., *Apiospora montagnei, Arthrinium arundinis, Ascochyta hordei, Asochyta graminea, Asochyta sorghi, Asocyhta tritici, Athelia rolfsii, Bipolaris sorokiniana, Blumeria graminis, Cephalosporium gramineum, Ceratobasidium cereale, Claviceps purpurea, Cochliobolus sativus, Colletotrichum graminicola, Drechslera graminea, Drechslera teres* f. *maculata, Drechslera teres, Drechslera wirreganensis, Erysiphe graminis* f. sp. *hordei, Fusarium culmorum, Fusarium graminearum, Fusarium nivale, Fusarium* spp., *Gaeumannomyces graminis* var. *tritici, Gibberella zeae, Glomerella graminicola, Helminthosporium tritici-repentis, Microdochium nivale, Monographella nivalis, Oidium monilioides, Phaeosphaeria avenaria* f. sp. *triticea, Pseudocercosoporella herpotrichoides, Pseudoseptoria donacis, Puccinia coronata, Puccinia graminis, Puccinia hordei, Puccinia striiformis, Pyrenophora teres, Pyre-nophora tritici-repentis, Pythium arrhenomanes, Pythium graminicola, Pythium iwayamai, Pythium okanoganense, Pythium paddicum, Pythium* spp., *Pythium tardicrescens, Rhizoctonia cerealis, Rhizoctonia solani, Rhynchosporium secalis, Sclerophthora rayssiae, Sclerotinia borealis, Sclerotium rolfsii, Selenophoma donacis, Septoria donacis, Septoria nodorum, Septoria passerinni, Sphacelia segetum, Stagonospora avenae* f. sp. *triticea, Stagonospora nodrum, Tapesia yallundae, Thanatephorus cucumeris, Tilletia controversa, Typhula idahoensis, Typhula incarnate, Typhula ishikariensis, Ustilago avenae, Ustilago hordei, Ustilago nigra, Ustilago nuda, Ustilago tritici, Verticillium dahliae.*

Another embodiment of the present invention relates to the use of the composition, which comprises (A) prothioconazole and (B) fluxapyroxad and (C) a further fungicidally active compound for controlling barley diseases caused by the above mentioned organisms.

Another embodiment of the present invention relates to the use of the composition, which comprises (A) prothioconazole and (B) fluxapyroxad for controlling rye or triticale, in particular rye, diseases caused by *Aecidium clematidis, Alternaria* spp., *Bipolaris sorokiniana, Cephalosporium gramineu-met* al., *Ceratobasidium cereale, Cercosporidium graminis, Cladosporium herbarum, Claviceps purpurea, Cochliobolus sativus, Colletotrichum graminicola, Coprinus psychromorbidus, Dilophospora alopecuri, Drechslera tritici-repentis, Epicoccum* spp., *Erysiphe graminis, Fusarium culmorum, Fusarium graminearum, Fusarium nivale, Fusarium* spp., *Gaeumaninomyces graministritici, Gibberella zeae, Glomerella graminicola, Helminthosporium sativum, Helminthosporium tritici-repentis, Hymenula cerealis, Leptosphaeria nodorum, Leptosphaeriaherpotrichoides, Microdochium nivale, Monographella nivalis, Mycosphaerella graminicola,*

*Mycosphaerella tassiana, Myriosclerotinia borealis, Neovossia indica, Phaeosphaeria herpotrichoides, Phaeosphaeria nodorum, Pseudocercosporella herpotrichoides, Pseudoseptoria donacis, Puccinia graminis, Puccinia recondita, Puccinia striiformis, Puccinia. graminis-secalis, Pyrenophora tritici-repentis, Pythium aphanidermatum, Pythium arrhenomanes, Pythium debaryanum, Pythium graminicola, Pythium ultimum, Rhizoctonia cerealis, Rhynchosporium secalis, Sclerotinia borealis, Scolicotrichum graminis, Selenophoma donacis, Septoria nodorum, Septoria secalis, Septoriatritici, Sphacelia segetum, Sporobolomyces spp., Stagonospora nodorum, Stemphylium spp., Tilletia caries, Tilletia controversa, Tilletia foetida, Tilletia indica, Tilletia laevis, Tilletia tritici, Typhula idahoensis, Typhula incarnata, Typhula ishikariensis, Typhula ishikariensis var. canadensis, Uredo glumarum, Urocystis occulta, Ustilago tritici.*

Another embodiment of the present invention relates to the use of the composition, which comprises (A) prothioconazole and (B) fluxapyroxad and (C) a further fungicidally active compound for controlling rye or triticale, in particular rye, diseases caused by the above mentioned organisms.

Another embodiment of the present invention relates to the use of the composition, which comprises (A) prothioconazole and (B) fluxapyroxad for controlling oats or millet, in particular millet, diseases caused by *Bipolaris sorokiniana, Bipolaris victoriae, Ceratobasidium cereale, Claviceps purpurea, Cochliobolus sativus, Cochliobolus victoriae, Colletotrichum graminicola, Drechslera avenacea, Drechslera avenae, Erysiphe graminis avenae, Erysiphe graminis, Fusarium culmorum, Fusarium graminearum, Fusarium nivale, Fusarium spp., Gaeumannomyces graminis var. avenae, Gaeumannomyces graminis, Gibberella zeae, Glomerella graminicola, Helminthosporium avenaceum, Helminthosporium avenae, Microdochium nivale, Monographella nivalis, Oidium monilioides, Phaeosphaeria avenaria, Puccinia coronata, Puccinia graminis, Pyrenophora avenae, Pythium debaryanum, Pythium irregulare, Pythium spp., Pythium ultimum, Rhizoctonia cerealis, Rhizoctonia solani, Sclerophthora macrosporaet al., Septoria avenae, Sphacelia segetum, Stagonospora avenae, Thanatephorus cucumeris, Typhula idahoensis, Typhula incarnata, Typhula ishikariensis, Ustilago avenae, Ustilago kolleri, Ustilago segetum.*

Another embodiment of the present invention relates to the use of the composition, which comprises (A) prothioconazole and (B) fluxapyroxad and (C) a further fungicidally active compound for controlling oats or millet, in particular millet, diseases caused by the above mentioned organisms.

Another embodiment of the present invention relates to the use of the composition, which comprises (A) prothioconazole and (B) fluxapyroxad for controlling soya bean diseases caused by *Acremonium, Alternaria spp., Arkoola nigra, Athelia rolfsii, Calonectria crotalariae, Cephalosporium gregatum, Cercospora kikuchii, Cercospora sojina, Chalara elegans, Choanephora infundibulifera, Choanephora trispora, Colletotrichum dematiumtruncatum, Colletotrichum destructivum, Colletotrichum truncatum, Corynespora cassiicola, Cylindrocladium crotalariae, Dactuliochaeta glycines, Dactuliophora glycines, Diaporthe phaseolorum, Diaporthe phaseolorum var. caulivora, Diaporthe phaseolorum var. sojae, Drechslera glycines, Fusarium solani, Fusarium spp., Glomerella glycines, Leptosphaerulina trifolii, Macrophomina phaseolina, Microsphaera diffusa, Mycoleptodiscus terrestris, Mycosphaerella usoenskajae, Neocosmospora vasinfecta, Peronospora manshurica, Phakopsora pachyrhizi, Phialophora gregata, Phomopsis phaseoli, Phomopsis sojae, Phomopsis spp., Phyllostictasojicola, Phymatotrichopsis omnivora, Phymatotrichum omnivorum, Phytophthora sojae, Pleospora tarda, Pyrenochaeta glycines, Pythium aphanidermatum, Pythium debaryanum, Pythium irregulare, Pythium myriotylum, Pythium ultimum, Rhizoctonia solani, Sclerotinia sclerotiorum, Sclerotium rolfsii, Septoria glycines, Spaceloma glycines, Stemphylium botryosum, Thanatephorus cucumeris, Thielaviopsis basicola.*

Another embodiment of the present invention relates to the use of the composition, which comprises (A) prothioconazole and (B) fluxapyroxad and (C) a further fungicidally active compound for controlling soya bean diseases caused by the above mentioned organisms.

Another embodiment of the present invention relates to the use of the composition, which comprises (A) prothioconazole and (B) fluxapyroxad for controlling rice diseases caused by *Achlya conspicua, Achlya klebsiana, Acrocylindrium oryzae, Alternaria padwickii, Athelia rolfsii, Ceratobasidium oryzae-sativae, Cercospora janseana, Cercospora oryzae, Cochiobolus lunatus, Cochliobolus miyabeanus, Cochliobolus miyabeanus, Curvularia lunata, Curvularia spp., Drechslera gigantean, Entyloma oryzae, Fusarium spp., Gaeumannomyces graminis, Magnaporthe grisea, Magnaporthe salvinii, Microdochium oryzae, Nakataea sigmoidae, Neovossia horrida, Pyricularia grisea, Pyricularia oryzae, Pythium dissotocum, Pythium spinosum, Pythium spp., Rhizoctonia oryzae, Rhizoctonia oryzae-sativae, Rhizoctonia solani, Rhynchosporium oryzae, Sarocladium oryzae, Sclerophthora macrospore, Sclerotium oryzae, Sclerotium rolfsii, Sphaerulina oryzina, Thanatephorus cucumeris, Tilletia barclayana, Ustilaginoidea virens.*

Another embodiment of the present invention relates to the use of the composition, which comprises (A) prothioconazole and (B) fluxapyroxad and (C) a further fungicidally active compound for controlling rice diseases caused by the above mentioned organisms.

Another embodiment of the present invention relates to the use of the composition, which comprises (A) prothioconazole and (B) fluxapyroxad for controlling com/maize diseases caused by *Acremonium strictum, Aspergillus flavus, Botryodiplodia theobromae, Botryosphaeria festucae, Cephalosporium acremonium, Cochliobolus cragrostidis, Cochliobolus intermedius, Cochliobolus lunatus, Cochliobolus pallescens, Cochliobolus tuberculatus, Colletotrichum graminicola, Corticium sasakii, Curvularia clavata, Curvularia eragrostidis, Curvularia inaequalis, Curvularia intermedia, Curvularia lunata, Curvularia maculans, Curvularia pallescens, Curvularia senegalensis, Curvularia tuberculata, Didymella exitalis, Diplodia frumenti, Diplodia macrospora, Diplodia maydis, Glomerella falcatum, Glomerella graminicola, Glomerella tucumanensis, Lasiodiplodia theobromae, Macrophomina phaseolina, Marasmiellus sp., Physoderma maydis, Rhizoctonia microsclerotia, Rhizoctonia solani, Stenocarpella macrospora, Thanatephorus cucumeris, Thanatephorus cucumeris*; or by downy mildews selected from *Alternaria alternata, Alternaria tenuis, Angiopsora zeae, Ascochyta ischaemi, Ascochyta maydis, Ascochyta tritici, Ascochyta zeicola, Aspergillus glaucus, Aspergillus niger, Aspergillus spp., Athelia rolfsii, Aureobasidium zeae, Bipolaris maydis, Bipolaris sorokiniana, Bipolaris victoriae, Bipolaris zeicola, Botryosphaeria festucae, Botryosphaeria zeae, Botryotinia fuckeliana, Botrytis cinerea, Cephalosporium maydis, Cephalotrichum stemonitis, Cercospora sorghi, Cercospora sorghi var. maydis, Cercospora zeae-maydis, Cladosporium cladosporioides, Cladosporium herbarum, Claviceps gigantea, Cochliobolus carbonum, Cochliobolus heterostrophus, Cochliobolus sativus, Cochliobolus victo-* riae, Cunninghamella sp., Curvularia pallescens, Dictochaeta fertilis, Diplodia frumenti, Diplodia macrospora, Diplodia maydis, Diplodia zeae, Doratomyces stemonitis, Drechslera prolata, Epicoccum nigrum, Exserohilum pedicellatum, Exserohilum prolatum, Exserohilum rostratum, Exserohilum turcicum, Fusarium acuminatum, Fusarium avenaceum, Fusarium culmorum, Fusarium episphaeria, Fusarium equiseti, Fusarium graminearum, Fusarium merismoides, Fusarium moniliforme, Fusarium moniliforme var. subglutinans, Fusarium oxysporum, Fusarium pallidoroseum, Fusarium poae, Fusarium roseum, Fusarium solani, Fusarium subglutinans, Fusarium sulphureum, Fusarium tricinctum, Gaeumannomyces graminis, Gibberella acuminata, Gibberella avenacea, Gibberella cyanogena, Gibberella fujikuroi, Gibberella intricans, Gibberella zeae, Gloeocercospora sorghi, Gonatobotrys simplex, Graphium penicillioides, Helminthosporium carbonum, Helminthosporium maydis, Helminthosporium pedicellatum, Helminthosporium rostratum, Helminthosporium sativum, Helminthosporium sorokinianum, Helminthosporium turcicum, Helminthosporium victoriae, Hormodendrum cladosporioides, Hyalothyridium maydis, Hypocrea sp., Kabatiella zeae, Khuskia oryzae, Leptosphaeria maydis, Leptothyrium zeae, Macrophoma zeae, Macrophomina phaseolina, Marianmaea elegans, Microdochium bolleyi, Monascus purpureus, Monascus ruber, Mucor sp., Mycosphaerella tassiana, Mycosphaerella zeae-maydis, Myrothecium gramineum, Nectria haematococca, Nigrospora oryzae, Ophiosphaerella herpotricha, Paraphaeosphaeria michotii, Penicillium chrysogenum, Penicilhum expansum, Penicillium oxalicum, Penicillium spp., Periconia circinata, Peronosclerospora maydis, Peronosclerospora philippinensis, Peronosclerospora sacchari, Peronosclerospora sorghi, Peronosclerospora spontanea, Phaeocytosporella zeae, Phaeocytostroma ambiguum, Phaeosphaeria maydis, Phoma sp., Phoma terrestris, Phomopsis sp., Phyllachora maydis, Phyllosticta maydis, Physalospora zeae, Physalospora zeicola, Physopella pallescens, Physopella zeae, Phytophthora cactorum, Phytophthora drechsleri, Phytophthora nicotianae var. parasitica, Pithomyces maydicus, Puccinia polysora, Puccinia sorghi, Pyrenochaeta terrestris, Pythium aphanidermatum, Pythium arrhenomanes, Pythium butleri, Pythium graminicola, Pythium spp., Rhizoctonia solani, Rhizoctonia zeae, Rhizoctonia zeae, Rhizopus arrhizus, Rhizopus microsporus, Rhizopus nigricans, Rhizopus stolonifer, Rhopographus zeae, Sclerophthora macrospore, Sclerophthora rayssiae var. zeae, Sclerospora graminicola, Sclerospora macrospore, Sclerospora maydis, Sclerospora philippinensis, Sclerospora sacchari, Sclerospora sorghi, Sclerospora spontanea, Sclerotium rolfsii, Scolecosporiella sp., Scopulariopsis brumptii, Selenophoma sp., Septoria zeae, Septoria zeicola, Septoria zeina, Setosphaeria pedicellata, Setosphaeria prolata, Setosphaeria rostrata, Setosphaeria turcica, Sphacelia sp., Sphacelotheca reiliana, Sphaerulina maydis, Spicaria sp., Sporisorium holci-sorghi, Stenocarpella macrospore, Stenocarpella maydis, Trichoderma lignorum, Trichoderma viride, Ustilaginoidea virens, Ustilago maydis, Ustilago zeae, Waitea circinate.

Another embodiment of the present invention relates to the use of the composition, which comprises (A) prothioconazole and (B) fluxapyroxad and (C) a further fungicidally active compound for controlling corn/maize diseases caused by the above mentioned organisms.

Another embodiment of the present invention relates to the use of the composition, which comprises (A) prothioconazole and (B) fluxapyroxad for controlling oil seed rape (including canola) diseases caused by Albugo canto dida, Albugo cruciferarum, Alternaria alternata, Alternaria brassicae, Alternaria brassicicola, Alternaria japonica, Alternaria raphani, Alternaria spp., Aphanomyces raphani, Ascochyta spp., Asteromella brassica, Athelia rolfsii, Botryotinia fuckeliana, Botrytis cinerea, Cercospora brassicicola, Cercosporella brassicae, Cladosporium sp., Colletotrichum gloeosporioides, Colletotrichum higginsianum, Cylindrosporium concentricum, Erysiphe cruciferarum, Erysiphe polygoni, Fusarium oxysporum, Fusarium oxysporum sp. conglutinans, Fusarium spp., Gliocladium roseum, Glomerella cingulata, Leptosphaeria maculans, Macrophomina phaseolina, Mycosphaerella brassicicola, Mycosphaerella capsellae, Nectria ochroleuca, Peronospora parasitica, Peronospora sp., Phoma lingam, Phymatotrichopsis omnivora, Phytophthora megasperma, Plasmodiophora brassicae, Pseudocercosporella capsellae, Pyrenopeziza brassicae, Pythium debaryanum, Pythium irregulare, Pythium spp., Rhizoctonia solani, Rhizopus stolonifer, Sclerotinia sclerotiorum, Sclerotium rolfsii, Thanatephorus cucumeris, Thanatephorus cucumeris, Urocystis brassicae, Verticillium longisporum.

Another embodiment of the present invention relates to the use of the composition, which comprises (A) prothioconazole and (B) fluxapyroxad and (C) a further fungicidally active compound for controlling oil seed rape (including canola) diseases caused by the above mentioned organisms.

Another embodiment of the present invention relates to the use of the composition, which comprises (A) prothioconazole and (B) fluxapyroxad for controlling pea diseases caused by Alternaria alternata, Aphanomyces euteiches f. sp. pisi, Ascochyta pinodella, Ascochyta pinodes, Ascochyta pisi, Botryotinia fuckeliana, Botrytis cinerea, Cercospora pisa-sativae, Chalara elegans, Cladosporium cladosporioides f. sp. pisicola, Cladosporium pisicola, Colletotrichum gloeosporioides, Colletotrichum pisi, Erysiphe pisi, Fusarium oxysporum, Fusarium oxysporumf sp. pisi, Fusarium solani, Fusicladium pisicola, Glomerella cingulata, Mycosphaerella pinodes, Oidium sp., Peronospora viciae, Phoma pinodella, Pythium spp., Rhizoctonia solani, Sclerotinia sclerotiorum, Septoria pisi, Thanatephorus cucumeris, Thielaviopsis basicola, Uromyces fabae.

Another embodiment of the present invention relates to the use of the composition, which comprises (A) prothioconazole and (B) fluxapyroxad and (C) a further fungicidally active compound for controlling pea diseases caused by the above mentioned organisms.

Another embodiment of the present invention relates to the use of the composition, which comprises (A) prothioconazole and (B) fluxapyroxad for controlling peanut diseases caused by Alternaria alternata, Alternaria arachidis, Alternaria tenuissima, Ascochyta adzamethica, Aspergillus flavus, Aspergillus niger, Aspergillus parasiticus, Athelia rolfsii, Bipolaris spicifera, Botryotinia fuckeliana, Botrytis cinerea, Calonectria crotalariae, Calonectria keyotensis, Cercospora arachidicola, Cercosporidium personatum, Chalara elegans, Choanephora spp., Cochliobolus spicifer, Colletotrichum arachidis, Colletotrichum dematium, Colletotrichum gloeosporioides, Colletotrichum mangenoti, Cristulariella moricola, Cylindrocladium crotalariae, Cylindrocladium scoparium, Diaporthe phaseolorum, Didymosphaeria arachidicola, Diplodia gossypina, Drechslera spicifera, Fusarium equiseti, Fusarium oxysporum, Fusarium scirpi, Fusarium solani, Fusarium spp., Gibberella intricans, Glomerella cingulata, Grovesinia pyramidalis, Lasiodiplodia theobromae, Leptosphaerulina crassiasca, Macrophomina phaseolina, Mycosphaerella arachidicola, Mycosphaerella arachidis, Mycosphaerella berkeleyi, Myrothecium roridum, Nectria haematococca, Oidium arachidis, Olpidium brassicae, Pestalotiopsis arachidis, Phaeoisariopsis personata, Phoma arachidicola, Phoma microspora, Phomopsis phaseoli, Phomopsis sojae, Phomopsis spp., Phyllosticta arachidis-hypogaea, Phyllosticta sojicola, Phymatotrichopsis omnivore, Phymatotrichum omnivorum, Pleosphaerulina sojicola, Pleospora tarda, Puccinia arachidis, Pythium aphanidermatum, Pythium debaryanum, Pythium irregulare, Pythium myriotylum, Pythium spp., Pythium ultimum, Rhizoctonia bataticola, Rhizoctonia solani, Rhizoctonia spp., Rhizopus spp., Sclerotinia minor, Sclerotinia sclerotiorum, Sclerotium cinnomomi, Sclerotium rolfsii, Sphaceloma arachidis, Stemphylium botryosum, Thanatephorus cucumeris, Thielaviopsis basicola, Verticillium albo-atrum, Verticillium dahliae.

Another embodiment of the present invention relates to the use of the composition, which comprises (A) prothioconazole and (B) fluxapyroxad and (C) a further fungicidally active compound for controlling peanut diseases caused by the above mentioned organisms.

Another embodiment of the present invention relates to the use of the composition, which comprises (A) prothioconazole and (B) fluxapyroxad for controlling sugar beet, fodder beet or beetroot diseases caused by *Alternaria brassicae, Alternaria alternata, Aphanomyces cochlioides, Aphanomyces cochlioides, Athelia rolfsii, Cercospora beticola, Choanephora cucurbitatum, Colletotrichum dematium* f. *spinaciae, Cylindrocladium, Erysiphe betae, Erysiphe polygoni, Fusarium oxysporum* f. sp. *betae, Fusarium oxysporum* f. sp. *spinaciae, Fusarium* spp., *Helicobasidium brebissonii, Macrophomina phaseolina, Peronospora farinosa* f. sp. *betae, Peronospora farinosa, Peronospora schachtii, Phoma betae, Phymatotrichopsis omnivora, Phymatotrichum omnivorum, Physarum cinereum, Physoderma leproides, Phytophthora drechsleri, Pleospora betae, Pleospora tarda, Puccinia subnitens, Pythium aphanidermatum, Pythium deliense, Pythium irregulare, Pythium* spp., *Ramulariabeticola, Rhizoctonia crocorum, Rhizoctonia solani, Rhizopus arrhizus, Rhizopus stolonifer, Sclerotinia sclerotiorum, Sclerotium rolfsii, Stemphylium botryosum, Thanatephorus cucumeris, Uromycesbetae, Urophlyctis leproides, Verticillium alboatrum.*

Another embodiment of the present invention relates to the use of the composition, which comprises (A) prothioconazole and (B) fluxapyroxad and (C) a further fungicidally active compound for controlling sugar beet, fodder beet or beetroot diseases caused by the above mentioned organisms.

Another embodiment of the present invention relates to the use of the composition, which comprises (A) prothioconazole and (B) fluxapyroxad for controlling potato diseases caused by *Aecidium cantensis, Alternaria alternata, Alternaria solani, Alternariatenuis, Angiosorus solani, Athelia rolfsii, Botryotinia fuckeliana, Botrytis cinerea, Cercospora concors, Cercospora solani, Cercospora solani-tuberosi, Choanephora cucurbitarum, Colletotrichum atramentarium, Colletotrichum coccodes, Dematophora* sp., *Erysiphe cichoracearum, Fusarium acuminatum, Fusarium avenaceum, Fusarium crookwellense, Fusarium culmorum, Fusarium equiseti, Fusarium oxysporum, Fusarium sambucinum, Fusarium solani* f. sp. *eumartii, Fusarium solani* var. *coeruleum, Fusarium* spp., *Fusarium sulphureum, Giberella pulicaris, Helminthosporium solani, Macrophomina phaseolina, Mycovellosiella concors, Phoma andigena* var. *andina, Phoma exigua* var. *exigua, Phoma exigua* var. *foveata, Phoma foveata, Phoma solanicola* f. *foveata, Phytophthora cryptogea, Phytophthora drechsleri, Phytophthora erythroseptica, Phytophthora infestans, Phytophthora megasperma, Phytophthora nicotianae* var. *parasitica, Phytophthora* spp., *Pleospora herbarum, Polyscytalum pustulans, Puccinia pittieriana, Pythium aphanidermatum, Pythium debaryanum, Pythium deliense, Pythium* spp., *Pythium ultimum* var. *ultimum, Rhizoctonia solani, Rosellinia* sp., *Sclerotinia sclerotiorum, Sclerotium bataticola, Sclerotium rolfsii, Septoria lycopersici* var. *malagutii, Spongospora subterranea* f. sp. *subterranea, Stemphylium herbarum, Synchytrium endobioticum, Thanatephorus cucumeris, Uloclodium atrum, Verticillium albo-atrum, Verticillium dahliae.*

Another embodiment of the present invention relates to the use of the composition, which comprises (A) prothioconazole and (B) fluxapyroxad and (C) a further fungicidally active compound for controlling potato diseases caused by the above mentioned organisms.

Another embodiment of the present invention relates to the use of the composition, which comprises (A) prothioconazole and (B) fluxapyroxad for controlling cotton diseases caused by *Alternaria alternata, Alternaria macrospora, Ascochyta gossypii, Ascochyta gossypii, Aspergillus flavus, Athelia rolfsii, Bipolaris spicifera, Botryosphaeria rhodina, Cercospora gossypina, Chalara elegans, Chalara elegans, Cochliobolus spicifer, Colletotrichumgossypii, Fusarium oxysporum* f. sp. *vasinfectum, Fusarium* spp., *Glomerella gossypii, Lasiodiplodia theobromae, Leveillula taurica, Macrophomina phaseolina, Mycosphaerella areola, Mycosphaerella gossypina, Myrothecium roridum, Nematospora* spp., *Nigrospora oryzae, Oidiopsis gossypii, Oidiopsis sicula, Phakopsora gossypii, Phoma exigua, Phymatotrichopsis omnivora, Phytophthora* spp., *Puccinia cacabata, Puccinia schedonnardi, Pythium* spp., *Ramularia gossypii, Rhizoctonia solani, Salmonia malachrae, Sclerotium rolfsii, Stemphylium solani, Thanatephorus cucumeris, Thielaviopsis basicola, Verticillium dahliae.*

Another embodiment of the present invention relates to the use of the composition, which comprises (A) prothioconazole and (B) fluxapyroxad and (C) a further fungicidally active compound for controlling cotton diseases caused by the above mentioned organisms.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as butane, propane, nitrogen and carbon dioxide. Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 per cent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 per cent by weight, 0.01 and 98 per cent by weight, preferable between 0.1 and 95 per cent by weight, particularly preferred between 0.5 and 90 per cent by weight of the active compound combination according to the invention, very particularly preferable between 10 and 70 per cent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The compositions according to the invention do not only comprise ready-to-use compositions which can be applied with suitable apparatus to the plant or the seed, but also commercial concentrates which have to be diluted with water prior to use.

The active compound combinations according to the invention can be present in (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and Semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

The invention furthermore comprises a method for treating seed. The invention furthermore relates to seed treated according to one of the methods described in the preceding paragraph.

The active compounds or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates in particular to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the mixtures according to the invention can be used in particular also for transgenic seed where the plant growing from this seed is capable of expressing a protein which acts against pests. By treating such seed with the active compound combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture or viticulture. In particular, this takes the form of seed of cereals (such as wheat, barley, rye, triticale, millet, oats), maize (corn), cotton, soya bean, rice, potatoes, sunflowers, beans, beets (e.g. sugar beets and fodder beets), peanuts, oilseed rape. The treatment of seeds of cereals (such as wheat, barley, rye, triticale, and oats), maize (corn), soya beans and rice is of particular importance.

As also described further below, the treatment of transgenic seed with the active compound combinations or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from Bacillus thuringiensis. In the context of the present invention, the active compound combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. Nos. 4,272,417 A, 4,245,432 A, 4,808,430 A, 5,876, 739 A, US 2003/0176428 A1, WO 2002/080675 A1, WO 2002/028186 A2.

The active compound combinations which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations which can be used according to the invention include all substances which promote wetting and are customary in the formulation of active agro-chemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbe-kämpfungsmittel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The active compounds or compositions according to the invention have strong microbicidal activity and can be used for controlling unwanted microorganisms, such as fungi and bacteria, in crop protection and material protection.

In crop protection, fungicides can be used for controlling *Plasmodiophoromycetes, Oomycetes, Chytridiomycetes, Zygomycetes, Ascomycetes, Basidiomycetes* and *Deuteromycetes*.

In crop protection, bactericides can be used for controlling *Pseudomonadaceae, Rhizobiaceae, Enterobacteriaceae, Corynebacteriaceae* and *Streptomycetaceae*.

The fungicidal compositions according to the invention can be used for the curative or protective control of phytopathogenic fungi. Accordingly, the invention also relates to curative and protective methods for controlling phytopathogenic fungi using the active compound combinations or compositions according to the invention, which are applied to the seed, the plant or plant parts, the fruit or the soil in which the plants grow. Preference is given to application onto the plant or the plant parts, the fruits or the soil in which the plants grow.

The compositions according to the invention for combating phytopathogenic fungi in crop protection comprise an active, but non-phytotoxic amount of the compounds according to the invention. "Active, but non-phytotoxic amount" shall mean an amount of the composition according to the invention which is sufficient to control or to completely kill the plant disease caused by fungi, which amount at the same time does not exhibit noteworthy symptoms of phytotoxicity. These application rates generally may be varied in a broader range, which rate depends on several factors, e.g. the phytopathogenic fungi, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and seed, and of the soil.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant variety protection rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds. Preference is given to the treatment of the plants and the above-ground and below-ground parts and organs of the plants, such as shoot, leaf, flower and root, examples which may be mentioned being leaves, needles, stems, trunks, flowers, and fruits.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material. They may be preferably employed as crop protection agents. They are active against normally sensitive and resistant species and against all or some stages of development.

The following plants may be mentioned as plants which can be treated according to the invention: cotton, Papilionaceae sp. (for example peas); major crop plants, such Gramineae sp. (for example maize, cereals such as wheat, rye, rice, barley, oats, millet and triticale), Asteraceae sp. (for example sunflowers), Brassicaceae sp. (for example oilseed rape), Fabacae sp. (for example beans, peas, peanuts), Papilionaceae sp. (for example soya beans), Solanaceae sp. (for example potatoes), Chenopodiaceae sp. (for example sugar beet, fodder beet, beet-root); and also in each case genetically modified varieties of these plants.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

The method of treatment according to the invention is used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down regulating or silencing other gene(s) which are present in the plant (using for example, antisense technology, co-suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in super-additive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses, Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in Brassica species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium Agrobacterium sp, the genes encoding a Petunia EPSPS, a Tomato EPSPS, or an Eleusine EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from Streptomyces species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidiny-oxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g. proteins from the VIP3Aa protein class; or 6) secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) hybrid insecticidal protein comprising parts from different secreted proteins from *Bacillus thuringiensis* or *Bacillus cereus*, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants
b. plants which contain a stress tolerance enhancing transgene capable of reducing the expression and/or the activity of the PARG encoding genes of the plants or plants cells.
c. plants which contain a stress tolerance enhancing transgene coding for a plant-functional enzyme of the nicotinamide adenine dinucleotide salvage synthesis pathway including nicotinamidase, nicotinate phosphori-bosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alteman,
3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:

a) Plants, such as cotton plants, containing an altered form of cellulose synthase genes,
b) Plants, such as cotton plants, containing an altered form of rsw2 or rsw3 homologous nucleic acids,
c) Plants, such as cotton plants, with increased expression of sucrose phosphate synthase,
d) Plants, such as cotton plants, with increased expression of sucrose synthase,
e) Plants, such as cotton plants, wherein the timing of the plasmodesmatal gating at the basis of the fiber cell is altered, e.g. through downregulation of fiberselective β 1,3-glucanase,
f) Plants, such as cotton plants, having fibers with altered reactivity, e.g. through the expression of N-acteylglucosaminetransferase gene including nodC and chitinsynthase genes.

Plants or plant cultivars (that can be obtained by plant biotechnology methods such as genetic engineering) which may also be treated according to the invention are plants, such as oilseed rape or related Brassica plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content,
b) Plants such as oilseed rape plants, producing oil having a low linolenic acid content,
c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B®(cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize)

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

In material protection the substances of the invention may be used for the protection of technical materials against infestation and destruction by undesirable fungi and/or microorganisms.

Technical materials are understood to be in the present context non-living materials that have been prepared for use in engineering. For example, technical materials that are to be protected against micro-biological change or destruction by the active materials of the invention can be adhesives, glues, paper and cardboard, textiles, carpets, leather, wood, paint and plastic articles, cooling lubricants and other materials that can be infested or destroyed by micro-organisms. Within the context of materials to be protected are also parts of production plants and buildings, for example cooling circuits, cooling and heating systems, air conditioning and ventilation systems, which can be adversely affected by the propagation of fungi and/or microorganisms. Within the context of the present invention, preferably mentioned as technical materials are adhesives, glues, paper and cardboard, leather, wood, paints, cooling lubricants and heat exchanger liquids, particularly preferred is wood. The combinations according to the invention can prevent disadvantageous effects like decaying, dis- and decoloring, or molding. The active compound combinations and compositions according to the invention can likewise be employed for protecting against colonization of objects, in particular ship hulls, sieves, nets, buildings, quays and signalling installations, which are in contact with sea water or brackish water.

The method of treatment according to the invention can also be used in the field of protecting storage goods against attack of fungi and microorganisms. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

In addition to the pathogens of fungal diseases mentioned above, which can be treated according to the invention, the following diseases may be mentioned by way of example, but not by way of limitation:

Powdery Mildew Diseases such as *Blumeria* diseases caused for example by *Blumeria graminis*; *Podosphaera* diseases caused for example by *Podosphaera leucotricha*; *Sphaerotheca* diseases caused for example by *Sphaerotheca fuliginea*; *Uncinula* diseases caused for example by *Uncinula necator*;

Rust Diseases such as *Gymnosporangium* diseases caused for example by *Gymnosporangium sabinae*; *Hemileia* diseases caused for example by *Hemileia vastatrix*; *Phakopsora* diseases caused for example by *Phakopsora pachyrhizi* and *Phakopsora meibomiae*; *Puccinia* diseases caused for example by *Puccinia recondita*, *Puccinia graminis* or *Puccinia striiformis*; *Uromyces* diseases caused for example by *Uromyces appendiculatus*;

Oomycete Diseases such as *Albugo* diseases caused for example by *Albugo candida*; *Bremia* diseases caused for example by *Bremia lactucae*; *Peronospora* diseases caused for example by *Peronospora pisi* and *Peronospora brassicae*; *Phytophthora* diseases caused for example by *Phytophthora infestans*;

*Plasmopara* diseases caused for example by *Plasmopara viticola*; *Pseudoperonospora* diseases caused for example by *Pseudoperonospora humuli* and *Pseudoperonospora cubensis*; *Pythium* diseases caused for example by *Pythium ultimum*;

Leaf spot, Leaf blotch and Leaf Blight Diseases such as *Alternaria* diseases caused for example by *Alternaria solani*; *Cercospora* diseases caused for example by *Cercospora beticola*; *Cladiosporium* diseases caused for example by *Cladiosporium cucumerinum*; *Cochliobolus* diseases caused for example by *Cochliobolus sativus* (Conidiaform: *Drechslera*, Syn: *Helminthosporium*) or *Cochliobolus miyabeanus*; *Colletotrichum* diseases caused for example by *Colletotrichum lindemuthianum*; *Cycloconium* diseases caused for example by *Cycloconium oleaginum*; *Diaporthe* diseases caused for example by *Diaporthe citri*; *Elsinoe* diseases caused for example by *Elsinoe fawcettii*; *Gloeosporium* diseases caused for example by *Gloeosporium laeticolor*; *Glomerella* diseases caused for example by *Glomerella cingulata*; *Guignardia* diseases caused for example by *Guignardia bidwellii*; *Leptosphaeria* diseases caused for example by *Leptosphaeria maculans* and *Leptosphaeria nodorum*; *Magnaporthe* diseases caused for example by *Magnaporthe grisea*; *Mycosphaerella* diseases caused for example by *Mycosphaerella graminicola*, *Mycosphaerella arachidicola* and *Mycosphaerella fijiensis*; *Phaeosphaeria* diseases caused for example by *Phaeosphaeria nodorum*; *Pyrenophora* diseases caused for example by *Pyrenophora teres* or *Pyrenophora tritici* repentis; *Ramularia*-diseases caused for example by *Ramularia collo-cygni* or *Ramularia areola*; *Rhynchosporium* diseases caused for example by *Rhynchosporium secalis*; *Septoria* diseases caused for example by *Septoria apii* and *Septoria lycopersici*; *Typhula* diseases caused for example by *Thyphula incamata*; *Venturia* diseases caused for example by *Venturia inaequalis*;

Root-, Sheath and Stem Diseases such as *Corticium* diseases caused for example by *Corticium graminearum*; *Fusarium* diseases caused for example by *Fusarium oxysporum*; *Gaeumannomyces* diseases caused for example by *Gaeumannomyces graminis*; *Rhizoctonia* diseases caused for example by *Rhizoctonia solani*; *Sarocladium* diseases caused for example by *Sarocladium oryzae*; *Sclerotium* diseases caused for example by *Sclerotium oryzae*; *Tapesia* diseases caused for example by *Tapesia acuformis*; *Thielaviopsis* diseases caused for example by *Thielaviopsis basicola*;

Ear and Panicle Diseases including Maize cob such as *Alternaria* diseases caused for example by *Alternaria* spp.; *Aspergillus* diseases caused for example by *Aspergillus flavus*; *Cladosporium* diseases caused for example by *Cladiosporium cladosporioides*; *Claviceps* diseases caused for example by *Claviceps purpurea*; *Fusarium* diseases caused for example by *Fusarium culmorum*; *Gibberella* diseases caused for example by *Gibberella zeae*; *Monographella* diseases caused for example by *Monographella nivalis*;

Smut—and Bunt Diseases such as *Sphacelotheca* diseases caused for example by *Sphacelotheca reiliana*; *Tilletia* diseases caused for example by *Tilletia caries*; *Urocystis* diseases caused for example by *Urocystis occulta*; *Ustilago* diseases caused for example by *Ustilago nuda*;

Fruit Rot and Mould Diseases such as *Aspergillus* diseases caused for example by *Aspergillus flavus*; *Botrytis* diseases caused for example by *Botrytis cinerea*; *Penicillium* diseases caused for example by *Penicillium expansum* and *Penicillium purpurogenum*; *Rhizopus* diseases caused by example by *Rhizopus stolonifer* *Sclerotinia* diseases caused for example by *Sclerotinia sclerotiorum*; *Verticillium* diseases caused for example by *Verticillium alboatrum*;

Seed—and Soilborne Decay, Mould, Wilt, Rot and Damping-off diseases caused for example by *Alternaria* diseases caused for example by *Alternaria brassicicola*; *Aphanomyces* diseases caused for example by *Aphanomyces euteiches*; *Ascochyta* diseases caused for example by *Ascochyta lentis*; *Aspergillus* diseases caused for example by *Aspergillus flavus*; *Cladosporium* diseases caused for example by *Cladosporium herbarum*; *Cochliobolus* diseases caused for example by *Cochliobolus sativus*; (Conidiaform: *Drechslera*, *Bipolaris* Syn: *Helminthosporium*); *Colletotrichum* diseases caused for example by *Colletotrichum coccodes*; *Fusarium* diseases caused for example by *Fusarium culmorum*; *Gibberella* diseases caused for example by *Gibberella zeae*; *Macrophomina* diseases caused for example by *Macrophomina phaseolina*; *Microdochium* diseases caused for example by *Microdochium nivale*; *Monographella* diseases caused for example by *Monographella nivalis*; *Penicillium* diseases caused for example by *Penicillium expansum*; *Phoma* diseases caused for example by *Phoma lingam*; *Phomopsis* diseases caused for example by *Phomopsis sojae*; *Phytophthora* diseases caused for example by *Phytophthora cactorum*; *Pyrenophora* diseases caused for example by *Pyrenophora graminea*; *Pyricularia* diseases caused for example by *Pyricularia oryzae*; *Pythium* diseases caused for example by *Pythium ultimum*; *Rhizoctonia* diseases caused for example by *Rhizoctonia solani*; *Rhizopus* diseases caused for example by *Rhizopus oryzae*; *Sclerotium* diseases caused for example by *Sclerotium rolfsii*; *Septoria* diseases caused for example by *Septoria nodorum*; *Typhula* diseases caused for example by *Typhula incarnata*; *Verticillium* diseases caused for example by *Verticillium dahliae*;

Canker, Broom and Dieback Diseases such as *Nectria* diseases caused for example by *Nectria galligena*; Blight Diseases such as *Monilinia* diseases caused for example by *Monilinia laxa*;

Leaf Blister or Leaf Curl Diseases including deformation of blooms and fruits such as *Exobasidium* diseases caused for example by *Exobasidium vexans*.

*Taphrina* diseases caused for example by *Taphrina deformans*;

Decline Diseases of Wooden Plants such as *Esca* disease caused for example by *Phaeomoniella clamydospora*, *Phaeoacremonium aleophilum* and *Fomitiporia mediterranea*; *Ganoderma* diseases caused for example by *Ganoderma boninense*; *Rigidoporus* diseases caused for example by *Rigidoporus lignosus*

Diseases of Flowers and Seeds such as *Botrytis* diseases caused for example by *Botrytis cinerea*;

Dispeases of Tubers such as *Rhizoctonia* diseases caused for example by *Rhizoctonia solani*; *Helminthosporium* diseases caused for example by *Helminthosporium solani*;

Club root diseases such as *Plasmodiophora* diseases, cause for example by *Plamodiophora brassicae*.

Diseases caused by Bacterial Organisms such as *Xanthomonas* species for example *Xanthomonas campestris* pv. *oryzae*; *Pseudomonas* species for example *Pseudomonas syringae* pv. *lachrymans*; *Erwinia* species for example *Erwinia amylovora*.

Preference is given to controlling the following diseases of soya beans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (*Basidiomycetes*) and against slime organisms and algae. Microorganisms of the following genera may be mentioned as examples: *Alternaria*, such as *Alternaria tenuis*, *Aspergillus*, such as *Aspergillus niger*, *Chaetomium*, such as *Chaetomium globosum*, *Coniophora*, such as *Coniophora puetana*, *Lentinus*, such as *Lentinus tigrinus*, *Penicillium*, such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*, *Escherichia*, l such as *Escherichia coli*, *Pseudomonas*, such as *Pseudomonas aeruginosa*, and *Staphylococcus*, such as *Staphylococcus aureus*.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The list of these fungi by no means limits the mycotic spectrum which can be covered, but is only for illustration.

When applying the compounds according to the invention the application rates can be varied within a broad range. The dose of active compound/application rate usually applied in the method of treatment according to the invention is generally and advantageously for treatment of part of plants, e.g. leaves (foliar treatment): from 0.1 to 10,000 g/ha, preferably from 50 to 1,000 g/ha, more preferably from 100 to 750g/ha; in case of drench or drip application, the dose can even be reduced, especially while using inert substrates like rockwool or perlite;

for seed treatment: from 2 to 250 g per 100 kg of seed, preferably from 3 to 200 g per 100 kg of seed, more preferably from 2.5 to 50 g per 100 kg of seed, even more preferably from 2.5 to 25 g per 100 kg of seed;

for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against pests and/or phytopathogenic fungi and/or microorganisms. The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

The application of the compositions according to the invention on growing plants or plant parts can also be used to protect plants or plant parts after harvesting.

According to the invention, post-harvest and storage diseases may be caused for example by the following fungi: *Colletotrichum* spp., e.g. *Colletotrichum musae, Colletotrichum gloeosporioides, Colletotrichum coccodes; Fusarium* spp., e.g. *Fusarium semitectum, Fusarium moniliforme, Fusarium solani, Fusarium oxysporum; Verticillium* spp., e.g. *Verticillium theobromae; Nigrospora* spp.; *Botrytis* spp., e.g. *Botrytis cinerea; Geotrichum* spp., e.g. *Geotrichum candidum; Phomopsis* spp., *Phomopsis natalensis; Diplodia* spp., e.g. *Diplodia citri; Alternaria* spp., e.g. *Alternaria citri, Alternaria altemata; Phytophthora* spp., e.g. *Phytophthora citrophthora, Phytophthora fragariae, Phytophthora cactorum, Phytophthora parasitica; Septoria* spp., e.g. *Septoria depressa; Mucor* spp., e.g. *Mucor piriformis; Monilinia* spp., e.g. *Monilinia fructigena, Monilinia laxa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fruiticola; Ceratocystis* spp., e.g. *Ceratocystis paradoxa; Penicillium* spp., e.g. *Penicillium funiculosum, Penicillium expansum, Penicillium digitatum, Penicillium italicum; Gloeosporium* spp., e.g. *Gloeosporium album, Gloeosporium perennans, Gloeosporium fructigenum, Gloeosporium singulata; Phlyctaena* spp., e.g. *Phlyctaena vagabunda; Cylindrocarpon* spp., e.g. *Cylindrocarpon mali; Stemphyllium* spp., e.g. *Stemphyllium vesicarium; Phacydiopycnis* spp., e.g. *Phacydiopycnis malirum; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Pezicula* spp.

According to the invention, post-harvest storage disorders are for example scald, scorch, softening, senescent breakdown, lenticel spots, bitter pit, browning, water core, vascular breakdown, $CO_2$ injury, $CO_2$ deficiency and $O_2$ deficiency.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2- und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxins, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The good fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", *Weeds* 1967, 15, 20-22):

If

X is the efficacy when active compound A is applied at an application rate of m ppm (or g/ha), Y is the efficacy when active compound B is applied at an application rate of n ppm (or g/ha), E is the efficacy when the active compounds A and B are applied at application rates of m and n ppm (or g/ha), respectively, and then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.*, 1964, 70, 73-80).

The invention is illustrated by the examples below. However, the invention is not limited to the examples.

Example: *Alternaria* Test (Tomatoes)/Preventive

Solvent: 24,5 parts by weight of acetone 24,5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application.

After the spray coating has dried on, the plants are inoculated with an aqueous spore suspenion of *Alternaria solani*. The plants are then placed in an incubation cabinet at approximately 20° C. and a relative atmospheric humidity of 100%. The test is evaluated 3 days after the inoculation. 0% means an efficacy which corresponds to that of the untreated control while an efficacy of 100% means that no disease is observed. The table below clearly shows that the observed activity of the active compound combination according to the invention is greater than the calculated activity, i.e. a synergistic effect is present. The difference between the biological activity found in the experiment and the activity calculated by using Colby's formula shows a clear superiority in synergism of the combination according to the invention compared to the known combination.

Results: *Alternaria* Test (Tomatoes)/preventive

| Active compounds | | Application rate of active compound in ppm a.i. | Efficacy in % found* | calc.** | diff.*** |
|---|---|---|---|---|---|
| (A) Prothioconazole | | 2 | 41 | | |
| | | 1 | 18 | | |
| | | 0.5 | 0 | | |
| (B) Fluxapyroxad | | 1 | 87 | | |
| | | 0.5 | 65 | | |
| | | 0.25 | 62 | | |
| Epoxiconazole | | 2 | 59 | | |
| | | 1 | 53 | | |
| | | 0.5 | 41 | | |
| known combination | | | | | |
| Epoxiconazole + (B) | 2:1 | 2 + 1 | 91 | 95 | −4 |
| | 4:1 | 2 + 0.5 | 87 | 86 | 1 |
| | 8:1 | 2 + 0.25 | 93 | 84 | 9 |
| Epoxiconazole + (B) | 1:1 | 1 + 1 | 94 | 94 | 0 |
| | 2:1 | 1 + 0.5 | 94 | 84 | 10 |
| | 4:1 | 1 + 0.25 | 88 | 82 | 6 |
| Epoxiconazole + (B) | 1:2 | 0.5 + 1 | 88 | 92 | −4 |
| | 1:1 | 0.5 + 0.5 | 88 | 79 | 9 |
| | 2:1 | 0.5 + 0.25 | 82 | 78 | 4 |
| combination according to the invention | | | | | |
| (A) + (B) | 2:1 | 2 + 1 | 94 | 92 | 2 |
| | 4:1 | 2 + 0.5 | 91 | 79 | 12 |
| | 8:1 | 2 + 0.25 | 88 | 78 | 10 |
| (A) + (B) | 1:1 | 1 + 1 | 94 | 89 | 5 |
| | 2:1 | 1 + 0.5 | 85 | 71 | 14 |
| | 4:1 | 1 + 0.25 | 81 | 69 | 12 |
| (A) + (B) | 1:2 | 0.5 + 1 | 94 | 87 | 7 |
| | 1:1 | 0.5 + 0.5 | 88 | 65 | 23 |
| | 2:1 | 0.5 + 0.25 | 90 | 62 | 28 |

*found = activity found

**calc. = activity calculated using Colby's formula

***diff. = difference between activity found and activity calculated using Colby's formula

The invention claimed is:

1. A method for controlling phytopathogenic fungi in soya bean, comprising applying a synergistic active compound combination comprising (A) prothioconazole and (B) fluxapyroxad to soya seed, soya plant, to fruit of a soya plant and/or to soil on which a soya plant grows or is supposed to grow, wherein the weight ratio of A:B is from 5:1 to 1:5, wherein (A) prothioconazole and (B) fluxapyroxad are the sole actives in the combination.

2. The method according to claim 1, wherein the soya plant, the fruit of a soya plant, or soil on which the soya plant grows or is intended to grow is treated.

3. The method according to claim 1, wherein soya plant leaves are treated in an amount from 0.1 to 10 000 g/ha.

4. A method according to claim 1, which controls soyabean disease caused by *Acremonium, Alternaria* spp., *Arkoola nigra, Athelia rolfsii, Calonectria crotalariae, Cephalosporium gregatum, Cercospora kikuchii, Cercospora sojina, Chalara elegans, Choanephora infundibulifera, Choanephora trispora, Colletotrichum dematiumtruncatum, Colletotrichum destructivum, Colletotrichum truncatum, Corynespora cassiicola, Cylindrocladium crotalariae, Dactuliochaeta glycines, Dactuliophora glycines, Diaporthe phaseolorum, Diaporthe phaseolorum* var. *caulivora, Diaporthe phaseolorum* var. *sojae, Drechslera glycines, Fusarium solani, Fusarium* spp., *Glomerella glycines, Leptosphaerulina trifolii, Macrophomina phaseolina, Microsphaera diffusa, Mycoleptodiscus terrestris, Mycosphaerella usoenskajae, Neocosmospora vasinfecta, Peronospora manshurica, Phakopsora pachyrhizi, Phialophora gregata, Phomopsis phaseoli, Phomopsis sojae, Phomopsis* spp., *Phyllostictasojicola, Phymatotrichopsis omnivora, Phymatotrichum omnivorum, Phytophthora sojae, Pleospora tarda, Pyrenochaeta glycines, Pythium aphanidermatum, Pythium debaryanum, Pythium irregulare, Pythium myriotylum, Pythium ultimum, Rhizoctonia solani, Sclerotinia sclerotiorum, Sclerotium rolfsii, Septoria glycines, Spaceloma glycines, Stemphylium botryosum, Thanatephorus cucumeris*, and/or *Thielaviopsis basicola*.

5. The method according to claim 1, wherein soya seed is treated, and 2 to 200 g of the combination per 100 kg of seed are employed.

6. The method according to claim 1, wherein soya seeds are treated.

7. The method according to claim 1, wherein soya seed of transgenic plants and/or transgenic soya plants are treated.

8. The method according to claim 1, wherein a soya plant is treated.

* * * * *